US006869280B2

(12) United States Patent
Fleischfresser

(10) Patent No.: US 6,869,280 B2
(45) Date of Patent: Mar. 22, 2005

(54) SUPPORT FOR MATERIAL TO BE FIRED FOR A CERAMIC DENTAL PROSTHESIS

(76) Inventor: Klaus Fleischfresser, Edenbergstr. 10A, DE-70329 Stuttgart (DE)

(*) Notice: Subject to any disclaimer, the term of this patent is extended or adjusted under 35 U.S.C. 154(b) by 0 days.

(21) Appl. No.: 10/684,144

(22) Filed: Oct. 10, 2003

(65) Prior Publication Data

US 2004/0137399 A1 Jul. 15, 2004

(30) Foreign Application Priority Data

Oct. 18, 2002 (DE) .......................................... 102 48 620
Jun. 4, 2003 (DE) .......................................... 103 25 524

(51) Int. Cl.$^7$ .............................................. F27D 5/00
(52) U.S. Cl. ...................... 432/259; 432/253; 269/54.5
(58) Field of Search ................................ 432/253, 258, 432/259; 269/53, 54.5

(56) References Cited

U.S. PATENT DOCUMENTS

| 3,861,867 A | * | 1/1975 | Ouhl .......................... 432/258 |
| 4,136,449 A | * | 1/1979 | Penrod et al. ................ 433/49 |
| 4,184,840 A | * | 1/1980 | Gamberg et al. ........... 432/253 |
| 5,941,700 A | * | 8/1999 | Fuchs ......................... 432/258 |

FOREIGN PATENT DOCUMENTS

DE 201 18 400 U1 4/2002

* cited by examiner

Primary Examiner—Gregory Wilson
(74) Attorney, Agent, or Firm—Pauley Petersen & Erickson

(57) ABSTRACT

A support for a material to be fired for a ceramic dental prosthesis, having a support plate dimensionally stable when heat is applied and having a plurality of passages which are arranged perpendicularly relative to the support plate surface. A bundle of several pins, which in an undeformed state extend parallel with each other, can be introduced into each one of the passages for placing the dental prosthesis to be fired on them.

21 Claims, 2 Drawing Sheets

SUPPORT FOR MATERIAL TO BE FIRED FOR A CERAMIC DENTAL PROSTHESIS

BACKGROUND OF THE INVENTION

1. Field of the Invention

This invention relates to a support for a material to be fired for a ceramic dental prosthesis, having a support plate which is dimensionally stable when heat is applied and having a plurality of passages, which are arranged perpendicularly relative to the support plate surface.

2. Description of Related Art

Such supports for materials to be fired are used in dental medicine for setting up the respective dental prosthesis and to place it into the firing chamber during repeatedly required firings in connection with the ceramic facing of a metal framing for a dental prosthesis, or complete replacement teeth made of a ceramic material. In this case it is necessary for the stable seating of the dental replacement to support the dental replacement on its inside facing away from the occlusal face on as many points as possible. Warp-free firing is thus assured, and the dental prosthesis to be fired is securely fixed in place.

In the prior art it is known to mount highly temperature-resistant metal pins on the support plate of the support for the material to be fired and to place the dental prosthesis on them. Each one of the metal pins must be matched to the shape of the inside of the dental prosthesis to be supported so that the metal pins are shortened to defined lengths and bent. The shortening requires a considerable effort. Furthermore, the arrangement of the shortened metal pins is only usable for the dental prosthesis which it matches.

German Patent Reference DE 201 18 400 U1 describes a support plate with a plurality of passages arranged perpendicularly relative to the surface of the support plate, into each of which a metal pin can be inserted. The metal pins are pushed from one side of the support plate through the passages until they contact on the other side of the support plate with the inside of the dental prosthesis to be fired. Then the metal pins are fixed in place by an adhesive. In this process the dental prosthesis is fixed, with the occlusal face down, in a deformable support material, while the support plate is maintained at a distance from the dental prosthesis. After successful contact, the arrangement is turned, so that the dental prosthesis is placed on the metal pins. The construction of such a support for material to be fired is elaborate and is matched to only one definitely shaped dental prosthesis.

SUMMARY OF THE INVENTION

It is one object of this invention to provide a support for material to be fired for a ceramic dental prosthesis which is particularly simply constructed and can be easily handled and delivers good firing results in the firing chamber.

This object is attained by a support for material to be fired having characteristics discussed in this specification and in the claims. Advantageous further developments of this invention are also discussed in this specification and in the claims.

A bundle, comprising several pins which, in the undeformed state extend parallel with each other, can be introduced into each one of the passages in the support plate for placing the dental prosthesis to be fired on them. With this step a plurality of pins is made available in the tightest space, namely already in the area of a single passage, which assure the secure placement of the dental prosthesis on them, because a multitude of points at the inside of the dental prosthesis can be supported.

An easy to apply, temperature-resistant adhesive can be used for securely fastening each bundle of pins inserted into a passage on the support plate, or in the respective passage.

However, alternatively the individual pins in a bundle cannot also be glued together, so that they can be easily pulled out of the support plate when required.

So that a bundle of pins can be easily inserted in a passage, the pins are kept in the bundle of pins together by a highly temperature-resistant connecting piece at one end. In this case the connecting piece can be designed so that it at least partially encloses the bundle of pins on one of its ends, in the manner of a ring. In addition, the connecting piece can be fixed in place on the bundle of pins by a temperature-resistant adhesive. Alternatively, the bundles of pins can also be welded to each other instead of having a connecting piece.

The secure placement of the dental prosthesis is necessary for introducing it into the firing chamber, which is achieved because a tip of each one of the pins can be brought into supportive contact with the molded interior of the dental prosthesis to be fired, which is located opposite its occlusal surface, wherein the dental prosthesis is seated at a distance away from the support plate by means of the pins. With such an arrangement, heat is not excessively carried off from the material to be fired.

In accordance with a particularly advantageous embodiment, the individual pins of each bundle can be bent away from each other, or fanned out in all spatial directions outside of the passages for a good supporting contact with the dental prosthesis to be fired.

The pins can be of tantalum or a highly temperature-resistant metal alloy like it, or of a highly temperature-resistant glass fiber material or ceramic material. Because of their dimensional stability, these materials assure warp-free firing. In order to achieve a particularly small amount of heat which is removed from the material to be fired, the pins can be made very thin, with a diameter between 0.2 mm and 0.7 mm.

So that the support plate, as well as the connecting piece at one end of the bundle of pins, are dimensionally stable during firing in the ceramic chamber, these components can be produced from a highly temperature-resistant metallic material, for example sinter material, from an aluminum oxide ceramic material, or a temperature and dimensionally stable ceramic material like that.

For being able to achieve a particularly large variability of the arrangement of the bundles of pins in the support plate, it is possible to arrange 50 to 150 passages per $cm^2$ in the support plate, which extend parallel with each other and perpendicular to the support plate surface. In this case the passages can have a circular, square or hexagonal cross-sectional face with a honeycomb structure.

BRIEF DESCRIPTION OF THE DRAWINGS

This invention is explained in greater detail in view of exemplary embodiments represented in the drawings.

DESCRIPTION OF PREFERRED EMBODIMENTS

Figure 1:
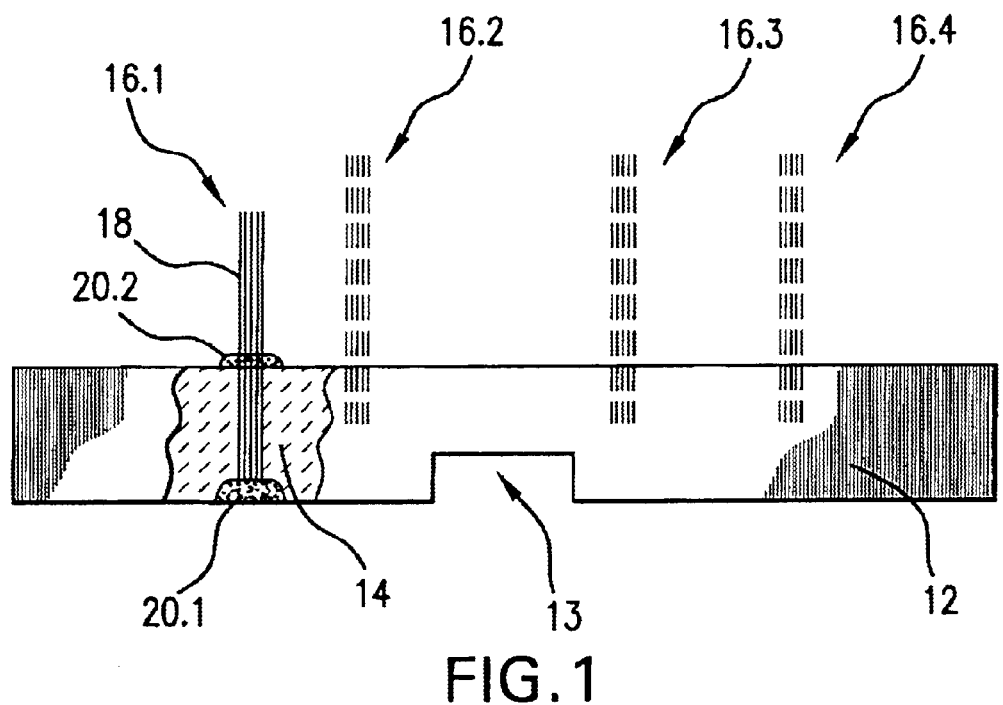
FIG. 1 is a schematic lateral partial sectional view of a support for material to be fired with glued-in bundles of pins.

A support for material to be fired for dental prostheses 10 is represented in a schematic lateral view in partial section, in FIG. 1. The support for the material to be fired has a substantially flat support plate 12, which is dimensionally stable when exposed to heat and has a multitude of passages 14 arranged perpendicularly to the support plate surface. The support plate 12 is approximately 5 mm high, but can also have different height dimensions.

The area around a passage 14 is shown in partial section in FIG. 1, wherein the immediately adjacent passages, which are separated from the passage 14 only by thin walls, are omitted from the drawing for reasons of clarity. The arrangement of the passages has essentially a type of honeycomb structure with square cross-sectional faces of each of the passages. However, the cross-sectional faces can also be arbitrarily designed, in particular circular or hexagonal. Because of the multitude of passages, there is a very large number of combination options regarding the arrangement of firing locations on the support for material to be fired.

A bundle 16.1, comprising three to six pins 18 which, in the undeformed state extend parallel with each other, for placing the dental prosthesis to be fired thereon, is inserted into the passage 14. Furthermore, bundles 16.2, 16.3 and 16.4 of pins are also indicated, which can be inserted into other arbitrary passages in the support plate 12.

The bundle 16.1 of pins inserted into the passage 14 is fixed in place in the passage 14 with a temperature-resistant adhesive 20.1 and 20.2. The lower and upper areas of the passage 14, into which the bundle 16.1 of pins is inserted, have an adhesive 20.1, or 20.2 for this purpose. The adhesive penetrates into the spaces between the pins 18, as well as into the passage 14, and fixes therein the bundle of pins. The adhesive used is a quick-setting ceramic two-component adhesive, which can be further cured at 300° C. to 500° C. and is also stable for ceramic firing in the higher temperature range.

However, alternatively the individual pins of a bundle can also not be glued together, so that they can be individually pulled out as required.

The support plate 12 also has a recess 13 formed out of its underside, which is used for providing an engagement point for a pair of oven tongs (not represented). With this feature it is possible to introduce the support plate 12 placed on a level surface, or the support for the material to be fired, into the firing chamber without tilting for firing.

Such an engagement possibility for a pair of oven tongs can also be provided if the bundles of pins protrude from the underside of the support plate so that the support plate 12 is placed with them on a surface. In that case the support plate 12 is seated spaced apart from the surface, so that the pair of oven tongs can act directly on the entire edge area of the support plate 12.

The support plate 12 is made of sinter metal, an aluminum oxide ceramic material, or a similar temperature and dimensionally stable ceramic material. 50 to 150, however preferably 90, passages 14 per $cm^2$ are arranged parallel with each other and extend perpendicularly with respect to the support plate surface in the support plate 12.

The pins 18 are of tantalum or a similar highly temperature-resistant metal alloy, or of a highly temperature-resistant glass fiber material or ceramic material, and each has a diameter between 0.2 mm to 0.7 mm, preferably 0.4 mm.

For firing the dental prosthesis, the support for the material to be fired is adapted to the temperature conditions inside the ceramic firing chamber. In this connection special care should be taken that no excessive amount of heat is removed via the pins from the dental prosthesis to be fired. The use of particularly thin pins effectively counteracts this heat loss. Because the support for material to be fired in accordance with this invention is employed instead of conventional supports for material to be fired, the volume which is thus reduced by the use of bundles of pins and possibly adhesive must be replenished up to the volume of conventional supports for material to be fired in order to obtain the same heat loss within the firing chamber.

Figure 2:
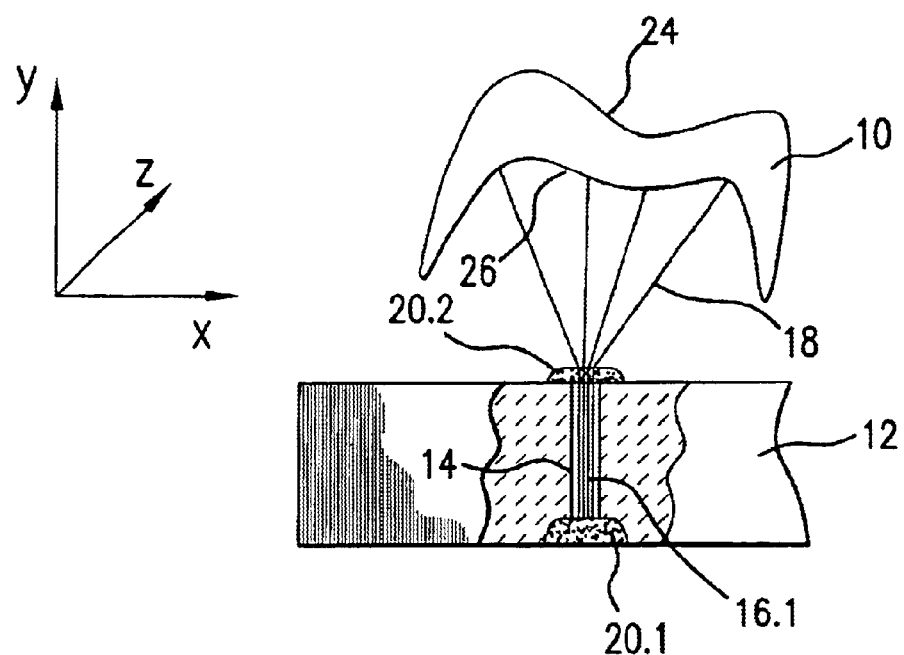
FIG. 2 is a schematic lateral partial sectional view of a support for material to be fired with a fanned-out bundle of pins and a dental prosthesis placed on it.
Figure 3:
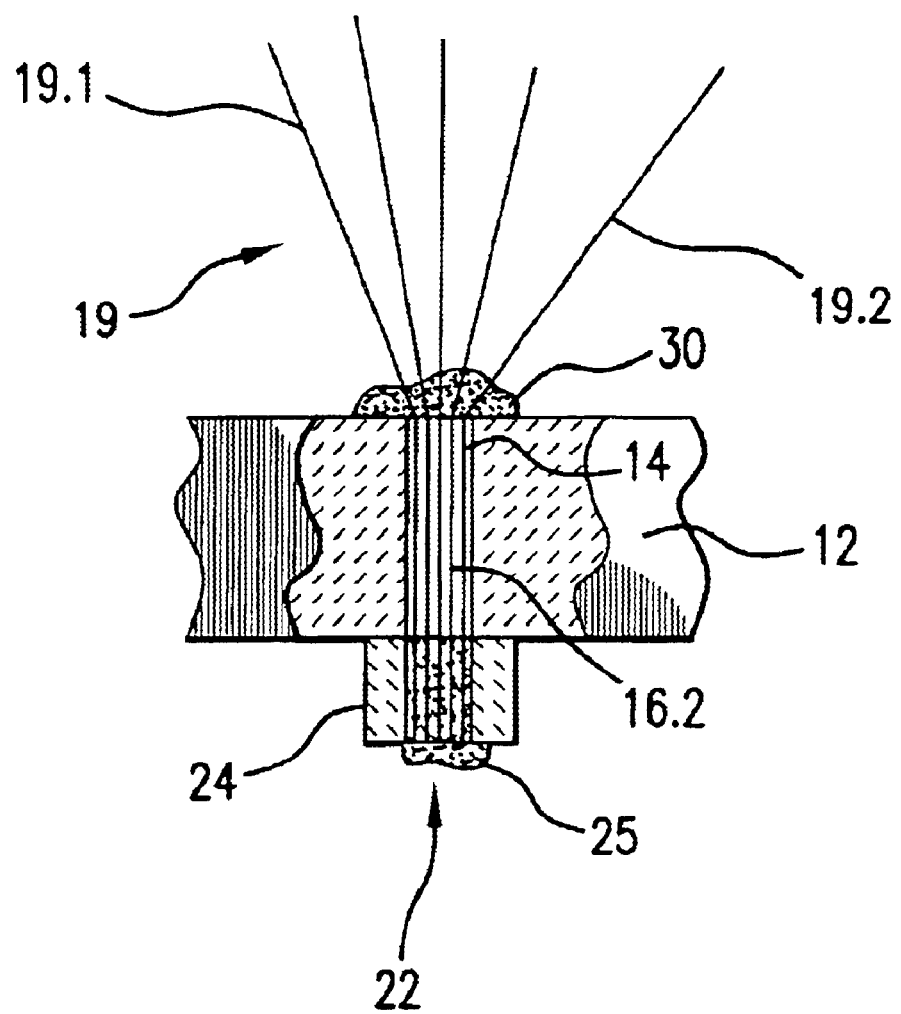
FIG. 3 is a schematic lateral partial sectional view of a support for material to be fired with a fanned-out bundle of pins, which is held together by a connecting piece at the other end.

A schematic lateral representation in partial section of a support for material to be fired with a fanned-out bundle 16.1 of pins and a dental prosthesis 20 placed on it is shown in FIG. 2. As already described in view of FIG. 1, the bundle 16.1 of pins is glued into the passage 14.

A tip of each one of the pins 18 of the bundle 16.1 of pins is brought into supportive contact with the molded interior 26 of the dental prosthesis 10 to be fired which is located opposite its occlusal surface 24. Thus, the dental prosthesis 10 is seated secure against tilting by the pins 18 substantially parallel with and at a distance from the support plate 12.

The pins 18 of the bundle 16.1 can be bent outside the passage 14 with respect to each other in all spatial directions x, y, z, or fanned out, manually or with the aid of pliers or tweezers (not represented). A good supporting contact with the dental prosthesis 10 to be fired, which is solidly seated, repeatedly supported on its underside, is thus achieved.

A schematic lateral representation in partial section of a support for material to be fired with a fanned-out bundle 16.2 of pins, which is kept together by a high temperature-resistant connecting piece 24 at the lower end 22. The connecting piece 24 encloses the bundle 16.2 of pins at its lower end 22 and is fixed in place on it by means of a temperature-resistant adhesive 25. Alternatively the connecting piece 24 can also rest tightly against the lower end 22 of the bundle 16.1 of pins so that in this area the pins 19 are maintained clampingly together. In this case the adhesive can be omitted, or the pins can be welded together at the one end.

The adhesive 30, which fixes the bundle of pins in place at the upper end of the passage 14, can also be omitted if the bundle 16.2 of pins is fixed in place perpendicularly to the support plate surface merely by the spreading or bending of at least the pins 19.1 and 19.2, which are on the outside of the passage 14, and possibly still further pins (not represented) of the bundle 16.2 of pins.

The connecting piece 24 can be made of sinter metal, an aluminum oxide ceramic material, or a similar temperature and dimensionally stable ceramic material.

An engagement possibility for oven tongs is also provided by the use of connecting pieces, because the bundles of pins with the connecting pieces protrude from the underside of the support plate 12 in such a way that the support plate 12 is seated at a distance from a surface. In that case the oven tongs can act directly on the entire edge area of the support plate 12.

German Patent References 102 48 620.4 and 103 25 524.9, the priority documents corresponding to this invention, and their teachings are incorporated, by reference, into this specification.

What is claimed is:

1. A support for a material to be fired for a ceramic dental prosthesis (10), having a support plate (12) which is dimensionally stable when heat is applied and having a plurality of passages (14) arranged perpendicularly relative to a support plate surface, the support comprising:

a bundle (16.1, 16.2, 16.3, 16.4) having a plurality of pins (18, 19) which in an undeformed state extend parallel with respect to each other is introducible into each of the passages (14) for placing the dental prosthesis (10) to be fired on the pins (18, 19), and the bundle (16.1) of the pins inserted into each of the passages(14) being fixable one of to the support plate (12) and on a respective passage (14) by a temperature-resistant adhesive (20.1, 20.2).

2. The support for the material to be fired in accordance with claim 1, wherein on an end the bundle (16.2) of the pins one of is maintained together by a high temperature-resistant connecting piece (24) and is welded together.

3. The support for the material to be fired in accordance with claim 2, wherein the pins of the bundle (16.2) of the pins are welded together at one end of the pins.

4. The support for the material to be fired in accordance with claim 3, wherein the connecting piece (24) at least one of at least partially encloses an end of the bundle (16.2) of the pins and is fixed in place on the end of the bundle (16.2) of the pins by a temperature-resistant adhesive (25).

5. The support for the material to be fired in accordance with claim 4, wherein a tip of each one of the pins (18) is supportively contactable with the dental prosthesis (10) to be fired at a molded inner surface (26) facing away from an occlusal surface (24), and the dental prosthesis (10) is seated at a distance from the support plate (12) by the pins (18).

6. The support for the material to be fired in accordance with claim 5, wherein for a supportive contact with the dental prosthesis (10) to be fired, the pins (18, 19) of the bundle (16.1, 16.2) are one of bendable outside of the passages (14) in spatial directions (x,y,z) with respect to each other and fanned open.

7. The support for the material to be fired in accordance with claim 6, wherein the pins (18, 19) are of one of tantalum, a high temperature-resistant metal alloy, and a high temperature-resistant glass fiber material or ceramic material.

8. The support for the material to be fired in accordance with claim 7, wherein each of the pins (18, 19) has a diameter between 0.2 mm and 0.7 mm.

9. The support for the material to be fired in accordance with claim 8, wherein at least one of the support plate (12) and the connecting piece (24) is of one of a high temperature-resistant metallic material, a sinter metal, an aluminum oxide ceramic material and a temperature and dimensionally stable ceramic material.

10. The support for the material to be fired in accordance with claim 9, wherein 50 to 150 of the passages (14) per $cm^2$ are arranged in the support plate (12), which extend parallel with respect to each other and perpendicular with respect to the support plate surface.

11. The support for the material to be fired in accordance with claim 10, wherein the passages (14) respectively have one of a circular, a square and a hexagonal cross-sectional face in a honeycomb structure.

12. A support for a material to be fired for a ceramic dental prosthesis (10), having a support plate (12) which is dimensionally stable when heat is applied and having a plurality of passages (14) arranged perpendicularly relative to a support plate surface, the support comprising:

a bundle (16.1, 16.2, 16.3, 16.4) having a plurality of pins (18, 19) which in an undeformed state extend parallel with respect to each other is introducible into each of the passages (14) for placing the dental prosthesis (10) to be fired on the pins (18, 19), and on an end the bundle (16.2) of the pins being one of maintained together by a high temperature-resistant connecting piece (24) and welded together.

13. A support for a material to be fired for a ceramic dental prosthesis (10), having a support plate (12) which is dimensionally stable when heat is applied and having a plurality of passages (14) arranged perpendicularly relative to a support plate surface, the support comprising:

a bundle (16.1, 16.2, 16.3, 16.4) having a plurality of pins (18, 19) which in an undeformed state extend parallel with respect to each other is introducible into each of the passages (14) for placing the dental prosthesis (10) to be fired on the pins (18, 19), and the pins of the bundle (16.2) of the pins welded together at one end of the pins.

14. A support for a material to be fired for a ceramic dental prosthesis (10), having a support plate (12) which is dimensionally stable when heat is applied and having a plurality of passages (14) arranged perpendicularly relative to a support plate surface, the support comprising:

a bundle (16.1, 16.2, 16.3, 16.4) having a plurality of pins (18, 19) which in an undeformed state extend parallel with respect to each other is introducible into each of the passages (14) for placing the dental prosthesis (10) to be fired on the pins (18, 19), and a connecting piece (24) at least one of at least partially encloses enclosing an end of the bundle (16.2) of the pins and being fixed in place on the end of the bundle (16.2) of the pins by a temperature-resistant adhesive (25).

15. The support for the material to be fired in accordance with claim 14, wherein a tip of each one of the pins (18) is supportively contactable with the dental prosthesis (10) to be fired at a molded inner surface (26) facing away from an occlusal surface (24), and the dental prosthesis (10) is seated at a distance from the support plate (12) by the pins (18).

16. A support for a material to be fired for a ceramic dental prosthesis (10), having a support plate (12) which is dimensionally stable when heat is applied and having a plurality of passages (14) arranged perpendicularly relative to a support plate surface, the support comprising:

a bundle (16.1, 16.2, 16.3, 16.4) having a plurality of pins (18, 19) which in an undeformed state extend parallel with respect to each other is introducible into each of the passages (14) for placing the dental prosthesis (10) to be fired on the pins (18, 19), and for a supportive contact with the dental prosthesis (10) to be fired, the pins (18, 19) of the bundle (16.1, 16.2) being one of bendable outside of the passages (14) in spatial directions (x,y,z) with respect to each other and fanned open.

17. The support for the material to be fired in accordance with claim 16, wherein the pins (18, 19) are of one of tantalum, a high temperature-resistant metal alloy, and a high temperature-resistant glass fiber material or ceramic material.

18. The support for the material to be fired in accordance with claim 16, wherein each of the pins (18, 19) has a diameter between 0.2 mm and 0.7 mm.

19. The support for the material to be fired in accordance with claim 16, at least one of the support plate (12) and a connecting piece (24) is of one of a high temperature-resistant metallic material, a sinter metal, an aluminum oxide ceramic material and a temperature and dimensionally stable ceramic material.

20. A support for a material to be fired for a ceramic dental prosthesis (10), having a support plate (12) which is dimensionally stable when heat is applied and having a plurality of passages (14) arranged perpendicularly relative to a support plate surface, the support comprising:

a bundle (16.1, 16.2, 16.3, 16.4) having a plurality of pins (18, 19) which in an undeformed state extend parallel with respect to each other is introducible into each of the passages (14) for placing the dental prosthesis (10) to be fired on the pins (18, 19), and 50 to 150 of the passages (14) per cm$^2$ being arranged in the support plate (12), which extend parallel with respect to each other and perpendicular with respect to the support plate surface.

21. The support for the material to be fired in accordance with claim 20, wherein the passages (14) respectively have one of a circular, a square and a hexagonal cross-sectional face in a honeycomb structure.

* * * * *